United States Patent
Shiratani (10) Patent No.: US 11,488,311 B2
(45) Date of Patent: Nov. 1, 2022

(54) DIAGNOSTIC IMAGING SUPPORT SYSTEM AND DIAGNOSTIC IMAGING APPARATUS

(71) Applicant: OLYMPUS CORPORATION, Hachioji (JP)

(72) Inventor: Fumiyuki Shiratani, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 22 days.

(21) Appl. No.: 17/138,385

(22) Filed: Dec. 30, 2020

(65) Prior Publication Data

US 2021/0118145 A1 Apr. 22, 2021

Related U.S. Application Data

(63) Continuation of application No. PCT/JP2018/028689, filed on Jul. 31, 2018.

(51) Int. Cl.
  *G06K 9/00* (2022.01)
  *G06T 7/11* (2017.01)
  *G06K 9/62* (2022.01)

(52) U.S. Cl.
  CPC .............. *G06T 7/11* (2017.01); *G06K 9/6267* (2013.01); *G06T 2207/10068* (2013.01)

(58) Field of Classification Search
  CPC ........ G06V 20/56; G06V 10/82; G06V 20/58; G06V 10/10; G06V 10/147; G06V 10/44; G06V 20/41; G06V 20/44; G06V 10/25; G06V 10/267; G06V 10/454; G06V 10/56; G06V 10/751; G06V 20/35; G06V 20/42;
  (Continued)

(56) References Cited

U.S. PATENT DOCUMENTS

| 10,360,474 B2 | 7/2019 | Shiratani |
| 10,491,813 B2 | 11/2019 | Shiratani |

(Continued)

FOREIGN PATENT DOCUMENTS

| JP | 2012254042 A | 12/2012 |
| JP | 2018515197 A | 6/2018 |
| WO | 2017042812 A2 | 3/2017 |

OTHER PUBLICATIONS

International Preliminary Report on Patentability (IPRP) (and English language translation thereof) dated Feb. 2, 2021 issued in International Application No. PCT/JP2018/028689.

(Continued)

*Primary Examiner* — Alex Kok S Liew
(74) *Attorney, Agent, or Firm* — Holtz, Holtz & Volek PC (57) ABSTRACT

A diagnostic imaging support system includes: an image input unit that receives an input of an image; a first processing unit that detects a region of interest including a subject of interest from the image, classifies the detected region of interest, and outputs a first classification result; and a second processing unit that subjects the region of interest to semantic segmentation, classifies the region of interest based on a result of the semantic segmentation, and outputs a second classification result. When a predetermined condition related to the region of interest is met, the first classification result is employed as indicating a class of the region of interest, and, when the condition is not met, the second classification result is employed as indicating the class of the region of interest.

4 Claims, 4 Drawing Sheets

(58) Field of Classification Search
CPC ...... G06V 20/49; G06V 20/52; G06V 20/597; G06V 20/70; G06V 40/162; G06V 40/168; G06V 40/172; G06V 40/20; G06N 3/0454; G06N 20/00; G06N 20/20; G06N 3/0445; G06N 3/08; G06N 7/005; G06N 3/006; G06N 3/04; G06N 3/0427; G06N 3/049; G06N 3/084; G06N 5/043
See application file for complete search history.

(56) References Cited

U.S. PATENT DOCUMENTS

| | | | |
|---|---|---|---|
| 10,860,930 B2 | 12/2020 | Shiratani | |
| 2005/0185835 A1* | 8/2005 | Matsugu | G06V 10/449 382/159 |
| 2005/0223574 A1* | 10/2005 | Fillatreau | G01C 17/38 33/356 |
| 2006/0222221 A1* | 10/2006 | Sathyanarayana | G06K 9/6292 382/128 |
| 2010/0172543 A1* | 7/2010 | Winkler | G08G 1/017 382/104 |
| 2014/0092228 A1 | 4/2014 | Usuba et al. | |
| 2018/0108138 A1 | 4/2018 | Kluckner et al. | |
| 2018/0253839 A1 | 9/2018 | Zur | |
| 2019/0065864 A1* | 2/2019 | Yu | G06V 20/56 |
| 2020/0074629 A1 | 3/2020 | Zur | |
| 2020/0342598 A1 | 10/2020 | Shiratani | |

OTHER PUBLICATIONS

International Search Report (ISR) (and English translation thereof) dated Oct. 16, 2018 issued in International Application No. PCT/JP2018/028689.

Dai, et al., "Instance-aware Semantic Segmentation via Multi-task Network Cascades", IEEE Conference on Computer Vision and Pattern Recognition, Jun. 27, 2016, pp. 3150-3158.

Terui, et al., "An Examination of Semantic Segmentation by Using Characteristics Information of Categories", IEICE Technical Report, Feb. 15, 2015, vol. 11, No. 455, pp. 119-124.

* cited by examiner

DIAGNOSTIC IMAGING SUPPORT SYSTEM AND DIAGNOSTIC IMAGING APPARATUS

CROSS-REFERENCE TO RELATED APPLICATIONS

This application is based upon and claims the benefit of priority from International Application No. PCT/JP2018/028689, filed on Jul. 31, 2018, the entire contents of which is incorporated herein by reference.

BACKGROUND OF THE INVENTION

1. Field of the Invention

The present invention relates to a diagnostic imaging support system and a diagnostic imaging support apparatus.

2. Description of the Related Art

Recently, attempts have been started to apply supervised learning represented by deep learning to diagnostic endoscopic imaging. In the related art, technologies to detect a pathological abnormality that is a subject of interest from an endoscopic image by means of a combination of the existent method and supervised learning have been proposed (patent document 1).

[Patent literature 1] WO2017/042812

Patent literature 1 discloses classifying (differentiating) a region of interest including the detected subject of interest by means of supervised learning but does not show awareness of an issue of classifying regions of interest with high precision or an attempt to address the issue. The inventors have delved for a technology capable of classifying regions of interest with high precision and have arrived at the present invention.

SUMMARY OF THE INVENTION

The present invention addresses the above-described issue, and a general purpose thereof is to provide a technology capable of classifying regions of interest with higher precision than in the related art.

A diagnostic imaging support system according to an embodiment of the present invention includes: an input unit that receives an input of an image; a first processing unit that detects a region of interest including a subject of interest from the image, classifies the detected region of interest, and outputs a first classification result; and a second processing unit that subjects the region of interest to semantic segmentation, classifies the region of interest based on a result of the semantic segmentation, and outputs a second classification result, wherein, when a predetermined condition related to the region of interest is met, the first classification result is employed as indicating a class of the region of interest, and, when the condition is not met, the second classification result is employed as indicating the class of the region of interest.

Another embodiment of the present invention relates to a diagnostic imaging support apparatus. The apparatus includes: an input unit that receives an input of an image; a first processing unit that detects a region of interest including a subject of interest from the image, classifies the detected region of interest, and outputs a first classification result; and a second processing unit that subjects the region of interest to semantic segmentation, classifies the region of interest based on a result of the semantic segmentation, and outputs a second classification result, wherein, when a predetermined condition related to the region of interest is met, the first classification result is employed as indicating a class of the region of interest, and, when the condition is not met, the second classification result is employed as indicating the class of the region of interest.

Another embodiment of the present invention relates to a diagnostic imaging support system. The diagnostic imaging support system includes: an input unit that receives an input of an image; a first processing unit that detects a region of interest including a subject of interest from an image derived from reducing a resolution of the image; a second processing unit that subjects a region, in an image having a higher resolution than the image derived from reducing the resolution, corresponding to the region of interest to semantic segmentation and classifies the region of interest based on a result of the semantic segmentation.

Optional combinations of the aforementioned constituting elements, and implementations of the invention in the form of methods, apparatuses, systems, recording mediums, and computer programs may also be practiced as additional modes of the present invention.

BRIEF DESCRIPTION OF THE DRAWINGS

Embodiments will now be described, by way of example only, with reference to the accompanying drawings which are meant to be exemplary, not limiting, and wherein like elements are numbered alike in several Figures, in which.

DETAILED DESCRIPTION OF THE INVENTION

The invention will now be described by reference to the preferred embodiments. This does not intend to limit the scope of the present invention, but to exemplify the invention.

Hereinafter, the invention will be described based on preferred embodiments with reference to the accompanying drawings.

First Embodiment

Figure 1:
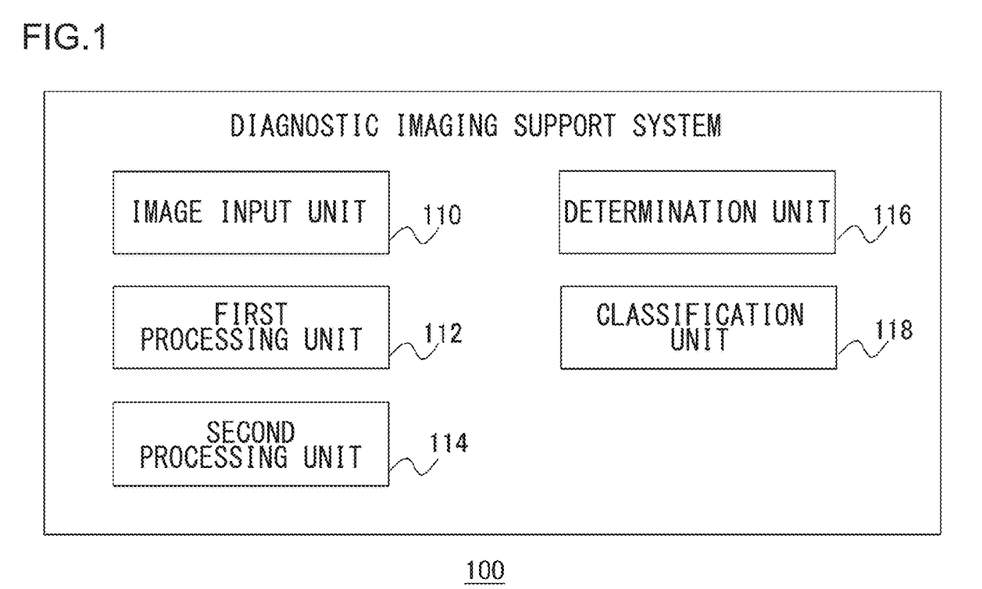
FIG. 1 is a block diagram showing the function and the configuration of an diagnostic imaging support system according to the first embodiment.

FIG. 1 is a block diagram showing the function and the configuration of an diagnostic imaging support system 100 according to the first embodiment. The blocks depicted here are implemented in hardware such as devices and mechanical apparatus exemplified by a CPU of a computer, and in software such as a computer program. FIG. 1 depicts functional blocks implemented by the cooperation of these elements. Therefore, it will be understood by those skilled in the art that the functional blocks may be implemented in a variety of manners by a combination of hardware and software. The same is also true of FIG. described later.

The diagnostic imaging support system 100 supports diagnosis of a pathological abnormality using an endoscopic image. An endoscopic image is taken by a related-art endoscope configured as a scope inserted into the body, a capsule endoscope, or a narrow band imaging (NBI) endoscope.

The diagnostic imaging support system 100 includes an image input unit 110, a first processing unit 112, a second processing unit 114, a determination unit 116, and an output unit 118.

The image input unit 110 receives an input of an endoscopic image from a user terminal or a further apparatus. The first processing unit 112 performs a detection process of detecting a pathological abnormality candidate region (region of interest) in the endoscopic image received by the image input unit 110. A pathological abnormality candidate region is a rectangular region including a pathological abnormality (subject of interest). The first processing unit 112 performs the first classification process of classifying (differentiating) the malignancy of the detected pathological abnormality candidate region (i.e., the pathological abnormality) and outputs the first classification result resulting from the classification.

More specifically, the first processing unit 112 feeds, in the detection process, an endoscopic image to a learning model for detection trained to detect a pathological abnormality candidate region including a pathological abnormality from the endoscopic image. The learning model for detection is preferably built as a neural network, and, more preferably, as a convolutional neural network such as a region proposal network (RPN). In other words, the first processing unit 112 preferably performs, in the detection process, a process using a neural network, and, more preferably, a convolutional neural network. Depending on the endoscopic image, a pathological abnormality candidate region may not be detected in the detection process, or one or a plurality of pathological abnormality candidate regions may be detected.

Further, the first processing unit 112 feeds, in the first classification process, information related to the detected pathological abnormality candidate region to a learning model for the first classification trained to classify pathological abnormality candidate regions. It is assumed here that the learning model for the first classification is trained to classify pathological abnormality candidate regions into benignant, slightly malignant, and malignant. The learning model for the first classification is preferably built as a neural network, and, more preferably, as a convolutional neural network such as a Fast R-CNN (FRCNN). In other words, the first processing unit 112 preferably performs, in the first classification process, a process using a neural network, and, more preferably, a convolutional neural network.

The second processing unit 114 performs semantic segmentation for classifying the malignancy of the pixels in the pathological abnormality candidate region detected by the detection process, i.e., classifying the pathological abnormality candidate region pixel by pixel. Further, the second processing unit 114 performs the second classification process for classifying the malignancy of the pathological abnormality candidate region based on the result of performing the semantic segmentation, i.e., the result of classifying the pixels, and outputs the second classification result resulting from the classification.

More specifically, the second processing unit 114 feeds information related to the detected pathological abnormality candidate region to a trained learning model for semantic segmentation. It is assumed here that the learning model for semantic segmentation is trained to classify the pixels of a pathological abnormality candidate region into benignant, slightly malignant, malignant, or normal. The learning model for semantic segmentation is preferably built as a neural network, and, more preferably, as a convolutional neural network such as a DeepLab. In other words, the second processing unit 114 preferably performs, in the second classification process, a process using a neural network, and, more preferably, a convolutional neural network.

Further, the second processing unit 114 defines, in the second classification process, the class with the largest number of pixels classified into a pathological abnormality (i.e., the pixels classified into benignant, slightly malignant, or malignant), as a classification result of the pathological abnormality candidate region (i.e., the pathological abnormality), i.e., as the second classification result.

The determination unit 116 determines which of the first classification result and the second classification result should be employed as indicating the class of the pathological abnormality candidate region. The first classification process classifies the pathological abnormality candidate region as a whole into a single category. If the area in the abnormality candidate region occupied by the pathological abnormality is small, and, more specifically, if the pathological abnormality is elongated in an oblique direction, therefore, the precision of classification tends to be low. In this background, the determination unit 116 determines to employ the first classification result yielded by the first classification process as indicating the class of the pathological abnormality candidate region in the case the area in the pathological abnormality candidate region occupied by the pathological abnormality is large. The determination unit 116 determines to employ the second classification result yielded by the second classification process as indicating the class of the pathological abnormality candidate region in the case the area in the pathological abnormality candidate region occupied by the pathological abnormality is small.

Figure 2A:
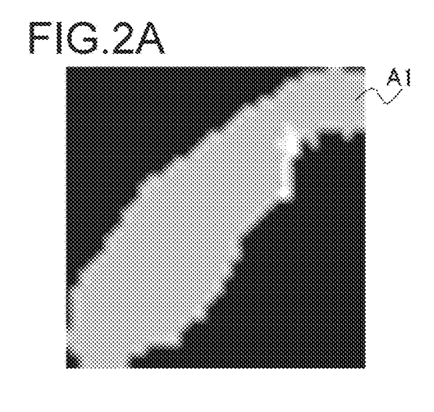
FIGS. 2A and 2B are diagrams for explaining the process by the determination unit of FIG. 1.
Figure 2B:
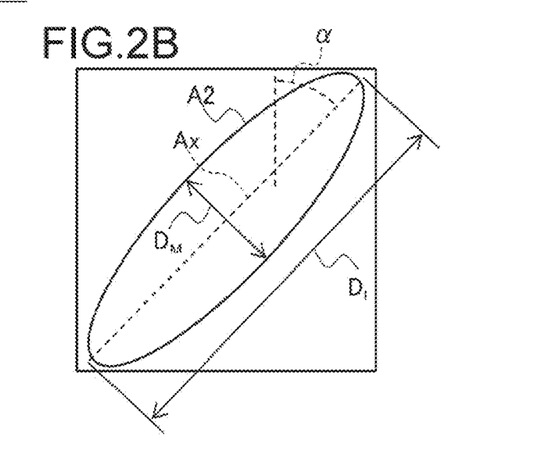

FIGS. 2A and 2B are diagrams for explaining the process by the determination unit 116. FIG. 2A shows a result of performing semantic segmentation. FIG. 2B shows an ellipse obtained by subjecting the pathological abnormality of FIG. 2A to elliptical approximation based on a publicly known method. The process performed by the determination unit 116 will be described in further detail with reference to FIG. 2A and FIG. 2B. The determination unit 116 first subjects a pathological abnormality region A1 resulting from performing semantic segmentation, i.e., the pathological abnormality region A1 that is a set of pixels classified as belonging to a pathological abnormality (i.e., benignant, slightly malignant, or malignant) by the semantic segmentation, to elliptical approximation. Subsequently, the determination unit 116 identifies the major diameter DL, the minor diameter DM, and the orientation of the major axis Ax of the pathological abnormality region A2 obtained by elliptical approximation. When the following condition is met, the determination unit 116 estimates that the pathological abnormality is no so elongated, or, if it is elongated, not elongated in an oblique direction and determines to employ the first classification result as indicating the class of the pathological abnormality candidate region. When the following condition is not met, on the other hand, the determination unit 116 estimates that the pathological abnormality is elongated to a certain degree or more in an oblique direction and determines to employ the second classification result as indicating the class of the pathological abnormality candidate region.

> minor diameter *DM*/major diameter *DL*≥threshold
> value *Th*1 (e.g., *Th*1=0.3)   (Condition)

or the acute angle α formed by the longitudinal direction of the image and the major axis Ax is within a predetermine angular range (e.g., 0°-30°)

The output unit 118 outputs the class determined by the determination unit 116 to be employed as indicating the class of the pathological abnormality candidate region to, for example, a display.

Figure 3:
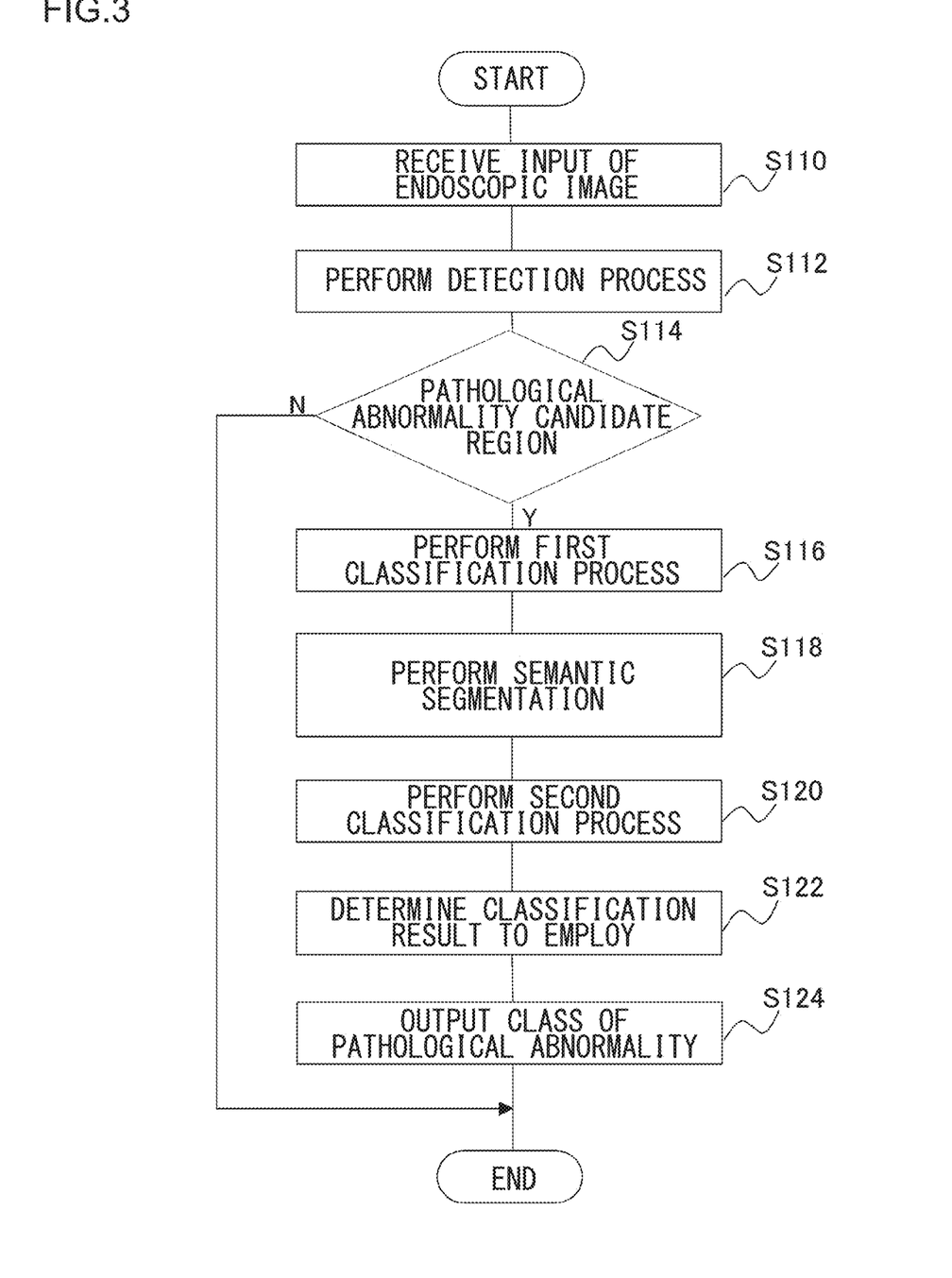
FIG. 3 is a flowchart showing an example of a series of steps in the diagnostic imaging support system according to the first embodiment.

Described above is the configuration of the diagnostic imaging support system 100. A description will now be given of the operation of the diagnostic imaging support system 100. FIG. 3 is a flowchart showing an example of a series of steps in the diagnostic imaging support system 100. The image input unit 110 receives an input of an endoscopic image (S110). The first processing unit 112 subjects the endoscopic image to a detection process for detecting a pathological abnormality candidate region (S112). When a pathological abnormality candidate region is detected, i.e., when a pathological abnormality candidate region is found in the endoscopic image (Y in S114), the first processing unit 112 subjects the detected pathological abnormality candidate region to the first classification process and outputs the first classification result (S116). The second processing unit 114 subjects the detected pathological abnormality candidate region to semantic segmentation (S118) and performs the second classification process for outputting the second classification result based on the result thereof (S120). The determination unit 116 determines to employ which of the first classification result and the second classification result should be employed as indicating the class of the pathological abnormality candidate region, based on the shape of the pathological abnormality region indicated by the result of performing the semantic segmentation (S122). The output unit 118 outputs the class determined to be employed (S124). When the pathological abnormality candidate region is not detected (N in S114), S116-S124 are skipped, and the process is terminated.

When a pathological abnormality candidate region is detected in the detection process of S112, the first classification process of S116 may be skipped, and control may proceed to the semantic segmentation of S118. When the semantic segmentation has been performed, the second classification process of S120 may be skipped, and control may proceed to the process of S122 of determining the classification result that should be employed. When it is determined to employ the first classification result, the first classification process of S116 may be performed. When it is determined to employ the second classification process, the second classification process of S120 may be performed.

In the above operation, it is assumed that the endoscopic image is a still image. In the case of moving images, the classification result may continue to be output depending on how the endoscopic images are read, and the process may be terminated at the end of the moving images.

According to the diagnostic imaging support system 100 according to the first embodiment described above, the second classification result is employed instead of the first classification result in the case the pathological abnormality in the pathological abnormality candidate region is elongated in an oblique direction, since the precision of classification of the first classification result tends to be low in that case. This improves the precision of classification.

Second Embodiment

In the first embodiment, a description is given of a case where a determination is made as to which of the first classification result and the second classification result should be employed as indicating the class of the pathological abnormality candidate region, based on the shape of the pathological abnormality indicated by the result of performing the semantic segmentation by the second processing unit. In the second embodiment, a description will be given of a case where a determination is made as to which of the first classification result and the second classification result should be employed as indicating the class of the pathological abnormality candidate region, based on the shape of the pathological abnormality candidate. The difference from the first embodiment will mainly be described.

When the pathological abnormality candidate region detected by the detection process by the first processing unit 112 has an elongated shape, it is estimated that the pathological abnormality included therein has an elongated shape. Meanwhile, a pathological abnormality often looks elongated when viewed laterally. The precision of the classification by the first processing unit 112 of a pathological abnormality imaged laterally tends to be low. Accordingly, the determination unit 116 determines to employ the first classification result yielded by the first classification process as indicating the class of the pathological abnormality candidate region in the case the pathological abnormality candidate region is shaped like a square or a rectangle that is not so elongated. In the case the pathological abnormality candidate region is shaped like rectangle elongated to a certain degree or more, the determination unit 116 determines to employ the second classification result yielded by the second classification process as indicating the class of the pathological abnormality candidate region.

More specifically, the determination unit 116 determines to employ the first classification result as indicating the class of the pathological abnormality candidate region when the following condition is met. When the following condition is not met, the determination unit 116 employs the second classification result as indicating the class of the pathological abnormality candidate region.

> length of shorter side of pathological abnormality
> candidate region/length of longer side of patho-
> logical abnormality candidate region≥threshold
> value *Th*2 (e.g., *Th*2=0.2)   (Condition)

Figure 4:
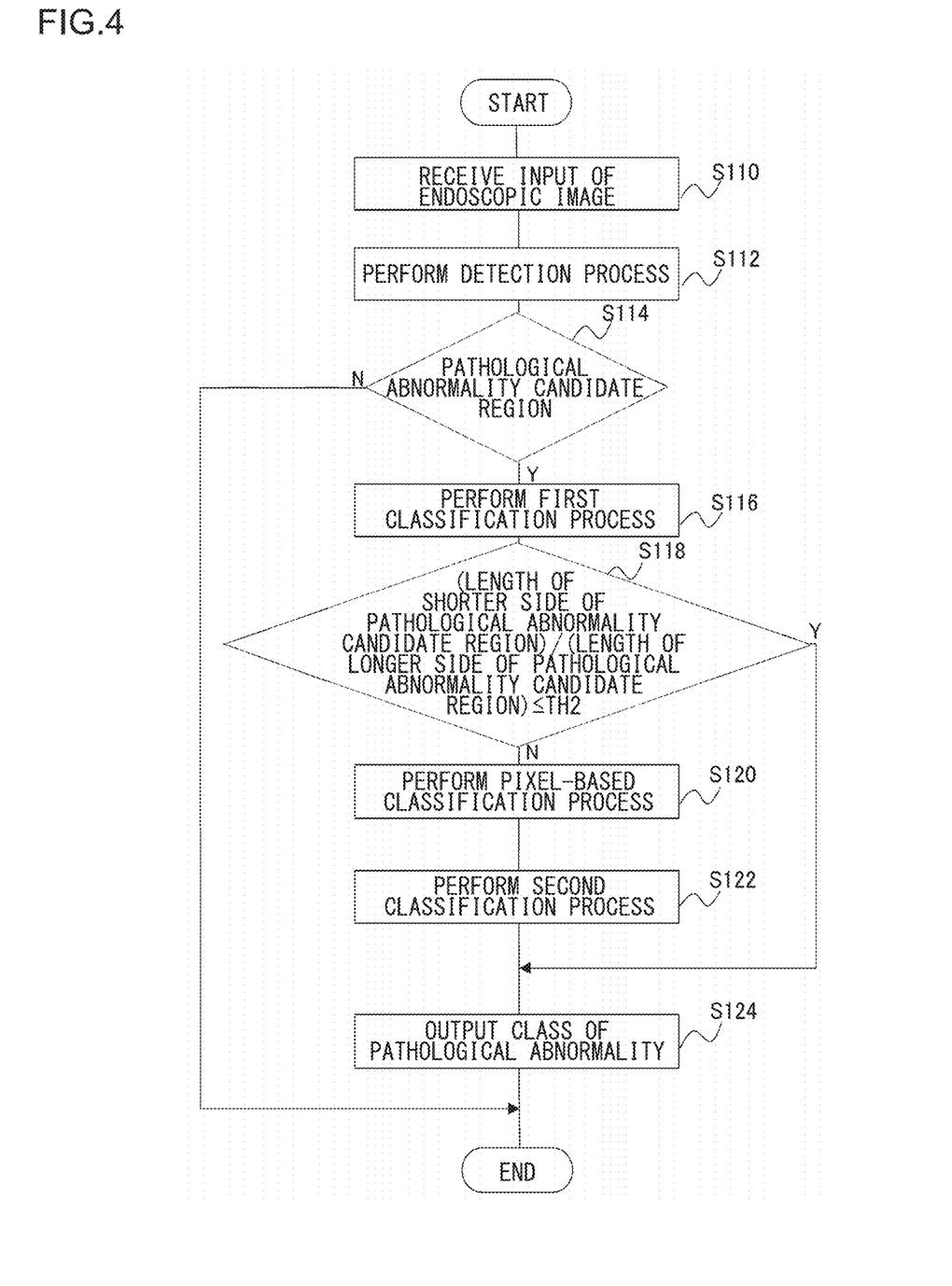
FIG. 4 is a flowchart showing an example of a series of steps in the diagnostic imaging support system according to the second embodiment.

A description will now be given of the operation of the diagnostic imaging support system. FIG. 4 is a flowchart showing an example of a series of steps in the diagnostic imaging support system according to the second embodiment. The difference from FIG. 3 will mainly be described below. When the first classification result is output, the determination unit 116 determines which of the first classification result and the second classification result should be employed as indicating the class of the pathological abnormality candidate region, based on the shape of the pathological abnormality candidate region (S118). When it is determined to employ the first classification result (Y in S118), the semantic segmentation of S120 and the second classification process of S122 are skipped, and the first classification result determined to be employed is output (S124). When it is determined to employ the second classification result (N in S118), the semantic segmentation and the second classification process are performed (S120, S122), and the second classification result is output as the result of classification (S124).

The step of S118 performed by the determination unit 116 may be performed immediately after the step of S114. In this case, the first classification process may be performed only when it is determined to employ the first classification result, and the second classification process may be performed only when it is determined to employ the second classification result.

In the case the pathological abnormality candidate area is shaped like a square or a rectangle close to a square, the pathological abnormality may be elongated in an oblique direction. Therefore, the technique of the first embodiment may be combined, and a further determination may be made as to which of the first classification result and the second classification result should be employed in the case the pathological abnormality candidate region is shaped like a square or a rectangle close to a square.

According to the diagnostic imaging support system according to the second embodiment described above, the second classification result is employed instead of the first classification result in the case the pathological abnormality candidate region is shaped like a rectangle elongated to a certain degree or more, since the precision of classification of the first classification result tends to be low in that case. This improves the precision of classification.

Third Embodiment

The inventors have corroborated that, denoting, at the time of learning, the output to which the SoftMax function is applied as the likelihood and denoting, at the time of recognition, the output to which the SoftMax function is not applied as the likelihood, there is correlation between the likelihood of classification and the precision of classification. In the third embodiment, a description will be given of a case where a determination is made as to which of the first classification result and the second classification result should be employed as indicating the class of the pathological abnormality candidate region, based on the likelihood of the first classification result and the likelihood of the second classification result. The difference from the first embodiment will mainly be described.

The first processing unit 112 performs the detection process and the first classification process. The determination unit 116 determines whether the likelihood of the first classification result yielded by the first classification process is equal to or greater than a predetermined threshold value Th3 (e.g., Th3=0.6). When the likelihood of the first classification result is equal to or greater than the threshold value Th3, the determination unit 116 determines to employ the first classification result as indicating the class of the pathological abnormality candidate region. When the likelihood of the first classification result is less than the threshold value Th3, the determination unit 116 determines not to employ the first classification result as indicating the class of the pathological abnormality candidate region. In this case, the second processing unit 114 performs the semantic segmentation and the second classification process. The determination unit 116 determines whether the likelihood of the second classification result yielded by the second classification process is equal to or greater than a predetermined threshold value Th4 (e.g., Th4=0.6). When the likelihood of the second classification result is equal to or greater than the threshold value Th4, the determination unit 116 determines to employ the second classification result as indicating the class of the pathological abnormality candidate region.

When the likelihood of the second classification result is less than the threshold value Th4, the determination unit 116 determines not to employ the second classification result as indicating the class of the pathological abnormality candidate region. In this case, the determination unit 116 determines that the pathological abnormality candidate region cannot be classified. The output unit 118 outputs the first classification result, the second classification result, or "unclassifiable".

The diagnostic imaging support system according to the third embodiment does not employ a less likely classification result and so improves the precision of classification.

Fourth Embodiment

Figure 5:
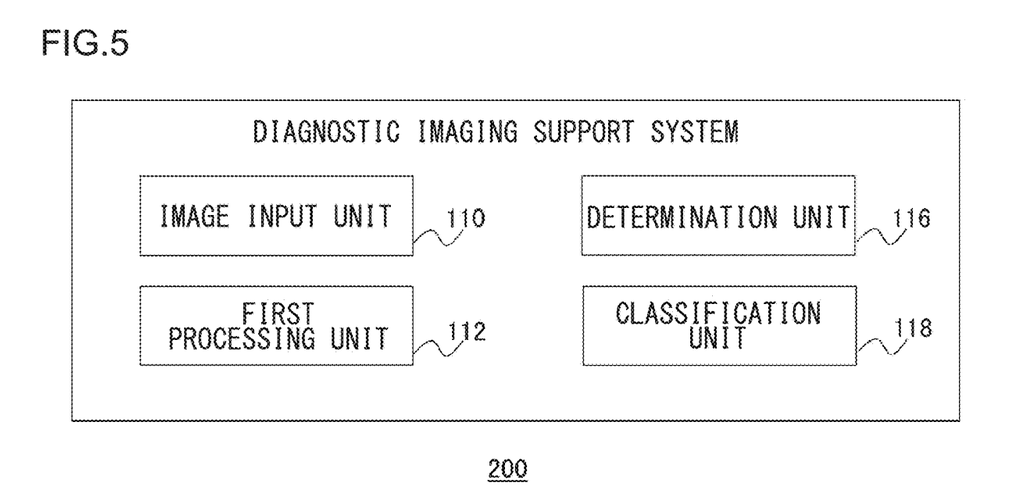
FIG. 5 is a block diagram showing the function and configuration of the diagnostic imaging support system according to the fourth embodiment.

FIG. 5 is a block diagram showing the function and configuration of a diagnostic imaging support system 200 according to the fourth embodiment. The difference from the first embodiment will mainly be described.

The diagnostic imaging support system 200 is not provided with a determination unit. The first processing unit 112 subjects an endoscopic image received by the image input unit 110 or an image derived from reducing the resolution of the received image to a detection process. The first processing unit 112 according to this embodiment does not perform the first classification process. The second processing unit 114 subjects a region in an image having a higher resolution than the image used in the detection process corresponding to the pathological abnormality candidate region, which is a region corresponding to the pathological abnormality candidate region detected by the detection process, to the second classification process. The output unit 118 outputs the second classification result yielded by the second classification process as indicating the class of the pathological abnormality candidate region.

The diagnostic imaging support system 200 according to the fourth embodiment described above detects a region of interest including a subject of interest from an image derived from reducing the resolution of an image and performs only the second classification process without performing the first classification process. Accordingly, it is possible to detect and classify a region of interest at an even higher speed.

Described above is an explanation of the present invention based on an exemplary embodiment. The embodiment is intended to be illustrative only and it will be understood by those skilled in the art that various modifications to combinations of constituting elements and processes are possible and that such modifications are also within the scope of the present invention.

In the embodiments, a description is given of a case where the diagnostic imaging support system 100 supports diagnosis of a pathological abnormality using an endoscopic image taken by an endoscope for medical use. The diagnostic imaging support system 100 can be applied, for example, to a case of supporting inspection of a damage on a metal surface using an endoscopic image taken by an industrial endoscope. To evaluate the seriousness of a damage, the diagnostic imaging support system may, for example, detect a region of interest that is a damage candidate region in the endoscopic image, identify a specular reflection region and a non-specular reflection region of the region of interest, extract an edge from the non-specular reflection region, calculate a level of blur of the edge, determine whether the region of interest is a region disqualified for diagnosis that accompanies a blur, based on the level of blur, perform a classification process of classifying the seriousness of a damage when the region of interest is not a region disqualified for diagnosis and output the classification result, and output, when the region of interest is a region disqualified for diagnosis, that the region of interest is a region disqualified for diagnosis without performing the classification process.

In the embodiments, a description is given of a case where the learning model for detection and the learning model for the first classification are built as separate learning models. However, these models may be built as a single learning model, and, preferably, as a single neural network, and, more preferably, as a single convolutional neural network such as FasterR-CNN.

The methods of the first-fourth embodiments may be combined arbitrarily so long as inconsistency does not occur.

In the embodiments and the variation, the diagnostic imaging support system may include a processor and a storage such as a memory. The functions of the respective parts of the processor may be implemented by individual hardware, or the functions of the parts may be implemented by integrated hardware. For example, the processor could include hardware, and the hardware could include at least one of a circuit for processing digital signals or a circuit for processing analog signals. For example, the processor may be configured as one or a plurality of circuit apparatuses (e.g., IC, etc.) or one or a plurality of of circuit devices (e.g., a resistor, a capacitor, etc.) packaged on a circuit substrate. The processor may be, for example, a central processing unit (CPU). However, the processor is not limited to a CPU. Various processors may be used. For example, a graphics processing unit (GPU) or a digital signal processor (DSP) may be used. The processor may be a hardware circuit comprised of an application specific integrated circuit (ASIC) or a field-programmable gate array (FPGA). Further, the processor may include an amplifier circuit or a filter circuit for processing analog signals. The memory may be a semiconductor memory such as SRAM and DRAM or may be a register. The memory may be a magnetic storage apparatus such as a hard disk drive or an optical storage apparatus such as an optical disk drive. For example, the memory stores computer readable instructions. The functions of the respective parts of the diagnostic imaging support system are realized as the instructions are executed by the processor. The instructions may be instructions of an instruction set forming the program or instructions designating the operation of the hardware circuit of the processor.

Further, in the embodiments and the variation, the respective processing units of the diagnostic imaging support system may be connected by an arbitrary format or medium of digital data communication such as communication network. Examples of the communication network include, for example, LAN, WAN, computers and networks forming the Internet.

What is claimed is:

1. A diagnostic imaging support system comprising:
a processor comprising hardware,
wherein the processor is configured to:
receive an input of an image;
detect a region of interest including a subject of interest from the image, classify the detected region of interest, and output a first classification result; and
subject the region of interest to semantic segmentation, classify the region of interest based on a result of the semantic segmentation, and output a second classification result, wherein:
when a predetermined condition related to a shape of the region of interest identified based on pixels classified by the semantic segmentation as belonging to the region of interest is met, the first classification result is employed as indicating a class of the region of interest, and, when the condition is not met, the second classification result is employed as indicating the class of the region of interest, and
the condition requires that a ratio of a minor diameter to a major diameter of an ellipse obtained by subjecting a set of pixels classified by the semantic segmentation as belonging to the region of interest to elliptical approximation be equal to or greater than a predetermined threshold value and that an acute angle formed by a major axis of the ellipse and a longitudinal direction of the image be within a predetermined angular range.

2. The diagnostic imaging support system according to claim 1, wherein each of an output of the first classification result and an output of the second classification result is implemented by performing a process using a convolutional neural network.

3. A non-transitory computer readable medium encoded with a program executable by a computer, the program being executable by the computer to cause the computer to perform functions comprising:
receiving an input of an image;
detecting a region of interest including a subject of interest from the image, classifying the detected region of interest, and outputting a first classification result; and
subjecting the region of interest to semantic segmentation, classifying the region of interest based on a result of the semantic segmentation, and outputting a second classification result,
wherein when a predetermined condition related to a shape of the region of interest identified based on pixels classified by the semantic segmentation as belonging to the region of interest is met, the first classification result is employed as indicating a class of the region of interest, and, when the condition is not met, the second classification result is employed as indicating the class of the region of interest;
the condition requires that a ratio of a minor diameter to a major diameter of an ellipse obtained by subjecting a set of pixels classified by the semantic segmentation as belonging to the region of interest to elliptical approximation be equal to or greater than a predetermined threshold value and that an acute angle formed by a major axis of the ellipse and a longitudinal direction of the image be within a predetermined angular range.

4. A diagnostic imaging method executed by a processor comprising hardware, the method comprising:
receiving an input of an image;
detecting a region of interest including a subject of interest from the image, classifying the detected region of interest, and outputting a first classification result; and
subjecting the region of interest to semantic segmentation, classifying the region of interest based on a result of the semantic segmentation, and outputting a second classification result,
wherein when a predetermined condition related to a shape of the region of interest identified based on pixels classified by the semantic segmentation as belonging to the region of interest is met, the first classification result is employed as indicating a class of the region of interest, and, when the condition is not met, the second classification result is employed as indicating the class of the region of interest, the condition requires that a ratio of a minor diameter to a major diameter of an ellipse obtained by subjecting a set of pixels classified by the semantic segmentation as belonging to the region of interest to elliptical approximation be equal to or greater than a predetermined threshold value and that an acute angle formed by a major axis of the ellipse and a longitudinal direction of the image be within a predetermined angular range.

* * * * *